United States Patent
Ye et al.

(10) Patent No.: US 9,286,701 B1
(45) Date of Patent: Mar. 15, 2016

(54) METHOD AND APPARATUS FOR ESTIMATING SCATTER IN A POSITRON EMISSION TOMOGRAPHY SCAN AT MULTIPLE BED POSITIONS

(71) Applicants: Kabushiki Kaisha Toshiba, Minato-ku (JP); Toshiba Medical Systems Corporation, Otawara-shi (JP)

(72) Inventors: Hongwei Ye, Kenosha, WI (US); Xiaofeng Niu, Mundelein, IL (US); Wenli Wang, Briarcliff Manor, NY (US)

(73) Assignees: Kabushiki Kaisha Toshiba, Minato-ku (JP); Toshiba Medical Systems Corporation, Otawara-shi (JP)

(*) Notice: Subject to any disclaimer, the term of this patent is extended or adjusted under 35 U.S.C. 154(b) by 33 days.

(21) Appl. No.: 14/471,989

(22) Filed: Aug. 28, 2014

(51) Int. Cl.
  *G06K 9/00* (2006.01)
  *G06T 11/00* (2006.01)
  *G01T 1/29* (2006.01)

(52) U.S. Cl.
  CPC ............. *G06T 11/005* (2013.01); *G01T 1/2985* (2013.01); *G06T 2207/10104* (2013.01)

(58) Field of Classification Search
  USPC .......................................................... 382/131
  See application file for complete search history.

(56) References Cited

U.S. PATENT DOCUMENTS

| | | | | |
|---|---|---|---|---|
| 7,336,760 B2* | 2/2008 | Virshup | ................. | A61B 6/032 378/207 |
| 8,193,505 B2* | 6/2012 | Watson | ................. | G01T 1/1647 250/363.03 |

OTHER PUBLICATIONS

Queiroz et al., "Dose Optimization in TOF-PET/MR Compared to TOF-PET/CT", PLOS, retrieved from the Internet on Nov. 20, 2015. Retrieved from <URL:http://journals.plos.org/plosone/article?id=10.1371/journal.pone.0128842>.*
Witherspoon et al., "Determination of Accuracy and Precision of Lesion Uptake Measurements in Human Subjects with Time-of-Flight PET", retrieved from Internet on Nov. 20, 2015. Retrieved from <URL:http://jnm.snmjournals.org/content/55/4/602.full>.*
Wollenweber, "Parameterization of a Model-Based 3D Whole-Body PET Scatter Correction".*
Roberto Accorsi et al., Optimization of a fully 3D single scatter simulation algorithm for 3D PET, Institute of Physics Publishing: Physics in Medicine and Biology, Published Jun. 2, 2004 (22 pages.).
C.S. Levin et al., A Monte Carlo Correction for the Effect of Compton Scattering in 3-D Pet Brain Imaging, IEEE Transactions on Nuclear Science, vol. 42, No. 4, Aug. 1995 (5 pages).
C.S. Levin et al., Removal of the Effect of Compton Scattering in 3-D Whole Body Positron Emission Tomography by Monte Carlo, IEEE 1996 (5 pages).

(Continued)

*Primary Examiner* — Gregory F Cunningham
(74) *Attorney, Agent, or Firm* — Oblon, McClelland, Maier & Neustadt, L.L.P.

(57) ABSTRACT

A method is provided for estimating scatter in a positron emission tomography (PET) scan at multiple bed positions, the method comprising calculating a first scatter sinogram based on scatter data obtained at a first bed position, calculating a second scatter sinogram based on scatter data obtained at a second bed position, and deriving a third scatter sinogram for a third bed position between the first bed position and the second bed position, wherein the third scatter sinogram is derived from the first scatter sinogram according to a first percentage of overlap of the first bed position with the third bed position, and from the second scatter sinogram according to a second percentage of overlap of the second bed position with the third bed position.

20 Claims, 16 Drawing Sheets

(56) References Cited

OTHER PUBLICATIONS

John M. Ollinger, Model-based scatter correction for fully 3D PET, Phys. Med. Biol. 41 (1996) 153-176, Printed in the UK (24 pages).

C.C. Watson et al, Evaluation of Simulation-Based Scatter Correction for 3-D PET Cardiac Imaging, IEEE Transactions on Nuclear Science, vol. 44, No. 1, Feb. 1997 (8 pages).

C.C. Watson, New, Faster, Image-Based Scatter Correction for 3D PET, IEEE Transactions on Nuclear Science, vol. 47, No. 4, Aug. 2000 (8 pages).

Charles C. Watson, Extension of Single Scatter Simulation to Scatter Correction of Time-of-Flight PET, IEEE Transactions on Nuclear Science, vol. 54, No. 5, Oct. 2007 (8 pages).

S.D. Wollenweber, Parameterization of a Model-Based 3D Whole-Body PET Scatter Correction, IEEE 2002 (5 pages).

\* cited by examiner

FIG. 7(B)
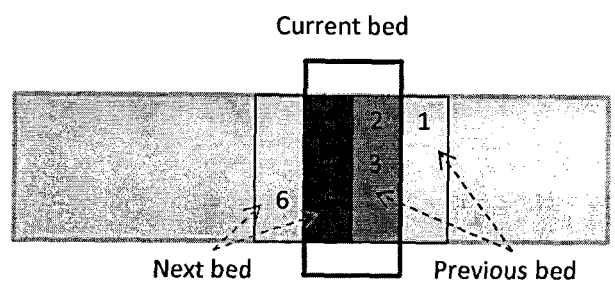
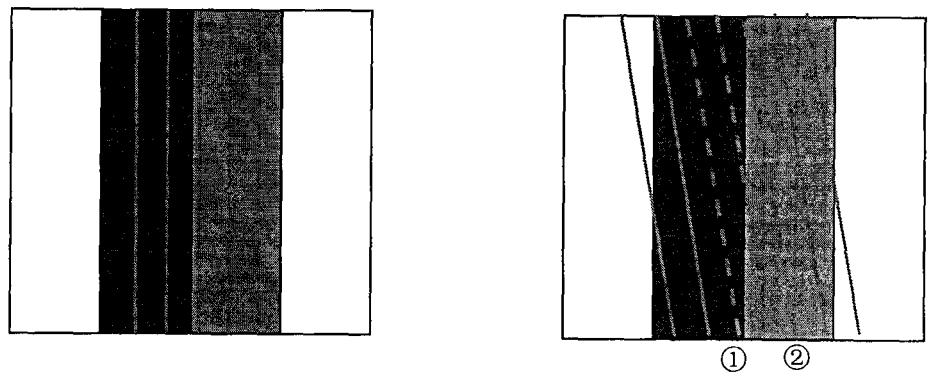
θ = 0, copy% = 100%   θ = -5.1, copy% ≈ 76%
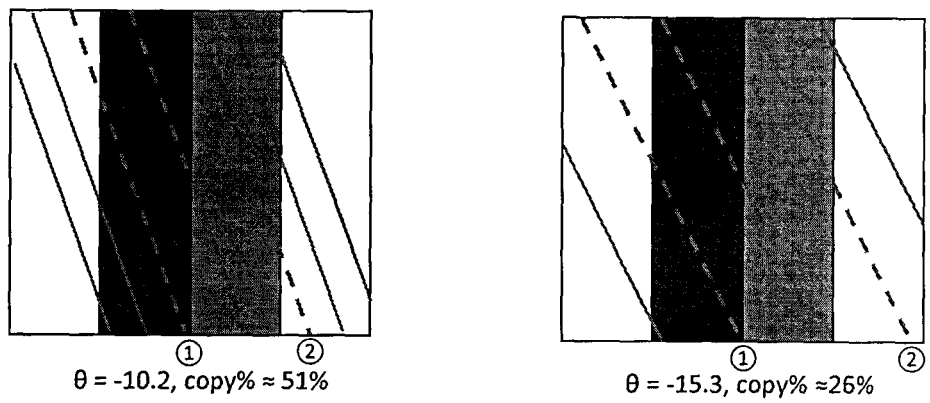
θ = -10.2, copy% ≈ 51%   θ = -15.3, copy% ≈ 26%

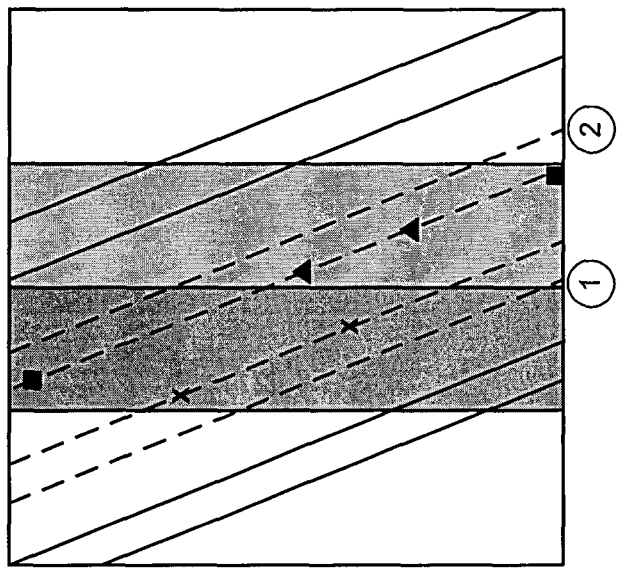

METHOD AND APPARATUS FOR ESTIMATING SCATTER IN A POSITRON EMISSION TOMOGRAPHY SCAN AT MULTIPLE BED POSITIONS

FIELD

The disclosed embodiments relate generally to scatter estimation in a positron emission tomography (PET) scan, and in particular, to a method for estimating scatter in a PET scan at multiple bed positions.

BACKGROUND

In three-dimensional PET scans, scatter is one of the most significant physical effects relating to the degradation of image quality. In typical PET systems, scatter events can be as much as 30%~50% of the total detected events in a PET scan. Image quality can be improved by correcting scatter events before or during image reconstruction.

There are several approaches for the correction of scatter events. Such approaches include a background subtraction or tail-fitting method, a convolution subtraction method, a Monte Carlo-based method, or a model-based scatter estimation (MBSE) including single scatter simulation (SSS). MBSE is a popular method used in modern PET systems and provides good scatter correction.

For a PET scan in a multi-bed position scanning system, bed positions that are adjacent to one another typically have at least 20% area overlap so as to achieve a more uniform axial sensitivity. To achieve good scatter estimation, MBSE requires the collection of scan data from bed positions that are adjacent to one another in order to estimate scatter that is out of the axial field of view (FOV).

However, extensive calculations are required when estimating scatter using the MBSE method. Even when a PET scan system has extremely high processing power with high optimization, scatter estimation suing the MBSE method can still take a long period of time because of the extensive calculations required. For example, a PET scan system for estimating scatter for typical patient data with 8 bed positions using a single 3.3 GHz CPU can take approximately 2500~4300 seconds/bed position, or 450 minutes.

As a result, it can be beneficial to reduce the processing time necessary to acquire reliable scatter estimation for the correction of scatter data and the reconstruction of PET data to improve image quality.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 7(B) illustrates bed positions with 4 different θ's with an amount of overlap of 50%;

FIG. 7(C) illustrates LORs of a bed position with θ=−10.2;

DETAILED DESCRIPTION

Figure 1A:
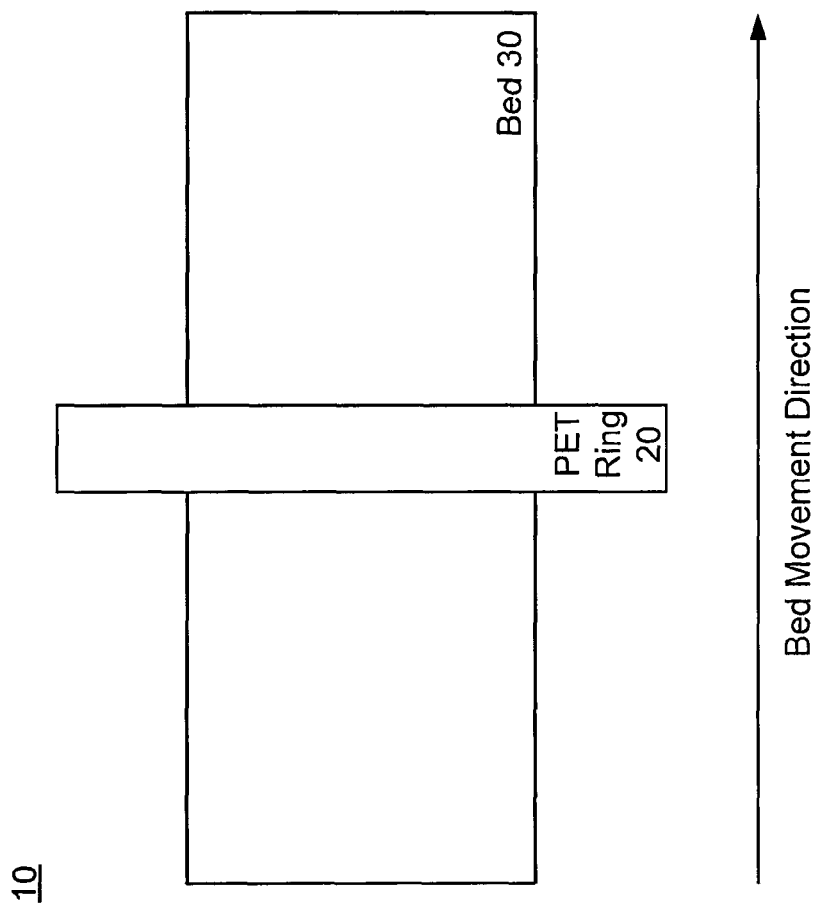
FIG. 1(A) illustrates an exemplary PET scanning system.

According to one embodiment, there is provided a method for estimating scatter in a positron emission tomography (PET) scan at multiple bed positions, the method comprising calculating a first scatter sinogram based on scatter data obtained at a first bed position, calculating a second scatter sinogram based on scatter data obtained at a second bed position, and deriving a third scatter sinogram for a third bed position between the first bed position and the second bed position, wherein the third scatter sinogram is derived from the first scatter sinogram according to a first percentage of overlap of the first bed position with the third bed position, and from the second scatter sinogram according to a second percentage of overlap of the second bed position with the third bed position.

In another embodiment, the step of deriving the third scatter sinogram comprises determining a first portion to copy, the first portion being equal to the first percentage of the first scatter sinogram, determining a second portion to copy, the second portion being equal to the second percentage of the second scatter sinogram, and copying the first portion and the second portion to the third scatter sinogram.

In another embodiment, the first scatter sinogram, the second scatter sinogram and the third scatter sinogram have the same dimensions as one another, and when a sum of the first percentage of overlap and the second percentage of overlap is less than 100%, the step of deriving the third scatter sinogram further comprises determining a remaining portion of the third scatter sinogram, the remaining portion having an area that is equal to a difference between an area of the third scatter sinogram and a sum of an area of the first portion and an area of the second portion, interpolating the remaining portion of the third scatter sinogram to create an interpolated portion, and copying the interpolated portion to the third scatter sinogram, wherein the third scatter sinogram includes the first portion, the second portion, and the interpolated portion.

In another embodiment, the first scatter sinogram, the second scatter sinogram and the third scatter sinogram have the same dimensions as one another, and when a sum of the first percentage of overlap and the second percentage of overlap is greater than 100%, the step of deriving the third scatter sinogram further comprises determining an overlapping portion of the third scatter sinogram, the overlapping portion including a first part of the first portion that overlaps with a second part of the second portion, averaging the first part and the second part of the overlapping portion to create an averaged portion, and copying the averaged portion to the third scatter sinogram, wherein the third scatter sinogram includes the averaged portion, a first remaining part of the first portion that does not include the first part, and a second remaining part of the second portion that does not include the second part.

In another embodiment, the step of copying the first portion and the second portion to the third scatter sinogram comprises determining a first position for the first portion in the third scatter sinogram, determining a second position for the second portion in the third scatter sinogram, and copying the first portion to the first position and the second portion to the second position, wherein a size of the third scatter sinogram is equal to a size of the first scatter sinogram and equal to a size of the second scatter sinogram.

In another embodiment, the step of copying the interpolated portion to the third scatter sinogram comprises determining a position for the interpolated portion in the third scatter sinogram, the position of the interpolated portion being determined based on positions of the first portion and the second portion, and copying the interpolated portion to the position in the third scatter sinogram.

In another embodiment, the step of copying the averaged portion to the third scatter sinogram comprises determining a position for the averaged portion in the third scatter sinogram, the position of the averaged portion being determined based on positions of the first portion and the second portion, and copying the averaged portion to the position in the third scatter sinogram.

In another embodiment, the first scatter sinogram and the second scatter sinogram are calculated using model-based scatter estimation (MBSE).

In another embodiment, the first scatter sinogram and the second scatter sinogram are calculated using Monte Carlo-based scatter estimation.

In another embodiment, the step of deriving the third scatter sinogram further rescaling the third scatter sinogram for the third bed position.

In another embodiment, the PET scan is performed with continuous bed movement.

In another embodiment, the PET scan is performed using step-and-shoot bed movement.

In another embodiment, the method further comprises determining each bed position within the multiple bed positions of the PET scan.

In another embodiment, the method further comprises determining the first percentage of overlap, and determining the second percentage of overlap.

Figure 1B:
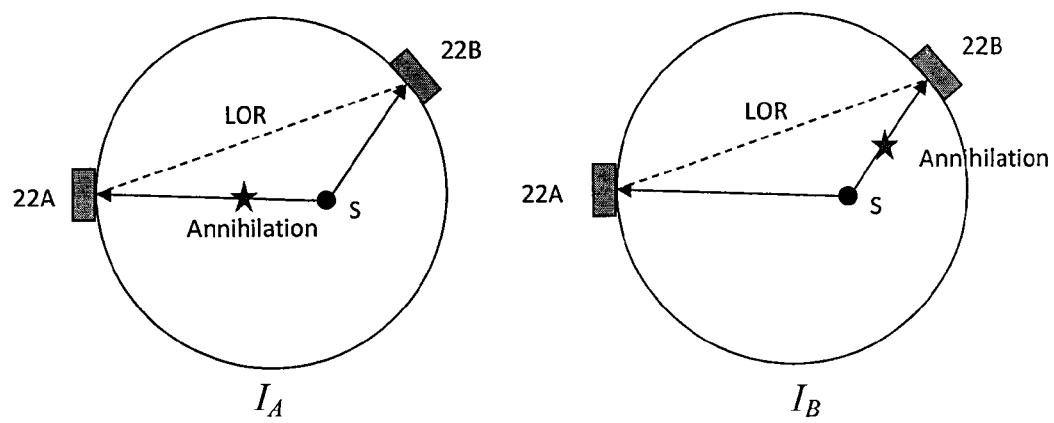
FIG. 1(B) illustrates exemplary detection of single scatter events by PET ring 20.

Referring now to the drawings, wherein like reference numerals designate identical or corresponding parts throughout the several views, FIG. 1(A) illustrates an exemplary PET scanning system. FIG. 1(B) illustrates exemplary detection of single scatter events in a PET ring.

As illustrated in FIG. 1(A), PET scanning system 10 includes PET ring 20 and bed 30. A scanning target, typically a patient, lies upon bed 30. Bed 30 moves through PET ring 20 in a bed movement direction. While FIG. 1(A) illustrates PET scanning system 10 that includes a single PET ring 20, PET scanning system 10 can include a plurality of PET ring 20.

As bed 30 moves through PET ring 20, position emission events are measured by PET ring 20 by detecting photons that are emitted when positrons and electrons collide and annihilate one another. Specifically, detectors 22A and 22B in PET ring 20 detect and measure the emission of photons as bed 30 moves through PET ring 20 of PET scanning system 10. Although FIG. 1(B) illustrates detectors 22A and 22B, each PET ring 20 can include more than two detectors 22.

In exemplary use of PET scanning system 10, bed 30 moves through PET ring 20 with a continuous movement motion, i.e., maintaining a constant speed. In such continuous motion, scan data is continuously collected by PET ring 20. Alternatively, bed 30 moves through PET scanning system 10 with a step-and-shoot motion, i.e., bed 30 stops at specific bed positions, stopping at each bed position for a predetermined period of time. With such a step-and-shoot motion, PET ring 20 collects scan data at each specific bed position. In other words, PET scanning system 10 collects scan data using either step-and-shoot or continuous bed movement.

Further, PET scanning system 10 can estimate scatter events using a time-of-flight (TOF) estimation method or a non-TOF estimation method.

All emission events detected by PET scanning system 10 are collected as bed 30 moves through PET scanning system 10. Once the PET scan is complete, PET scanning system 10 processes the collected scan data to reconstructs an image from the collected scan data by correcting the scatter data.

To correct the scatter data, PET scanning system 10 estimates scatter by using the MBSE method. Alternatively, PET scanning system 10 can estimate scatter by using methods such as the Monte Carlo scatter estimation method, background subtraction method or convolution subtraction method.

The MBSE method considers and models the physics of Compton scattering in a system by a mathematical model to calculate single scatter events, and a typical example is SSS. In one embodiment, PET scanning system 10 calculates single scatter events utilizing physical effects such as inter-crystal scattering and photo penetration in crystals, positron ranges, non-colinearity, multiple scatter events, accurate photon attenuation, etc. However, an exemplary embodiment of PET scanning system 10 reduces computational time by solely calculating scatter events. To compensate for the difference between model and real systems, a tail-fitting or other method is applied.

In an exemplary embodiment, PET scanning system 10 utilizes known SSS formula to calculate single scatter events.

To accurately collect scan data, bed positions can theoretically overlap anywhere from 0% to 100%. In other words, bed positions do not overlap at a value of 0%, and bed positions completely overlap at a value of 100%. Practically, PET scanning system 10 benefits from an existence of at least some bed position overlap, i.e. an overlap of more than 0%, by an increase in uniform axial sensitivity.

Figures 2A, 2B:
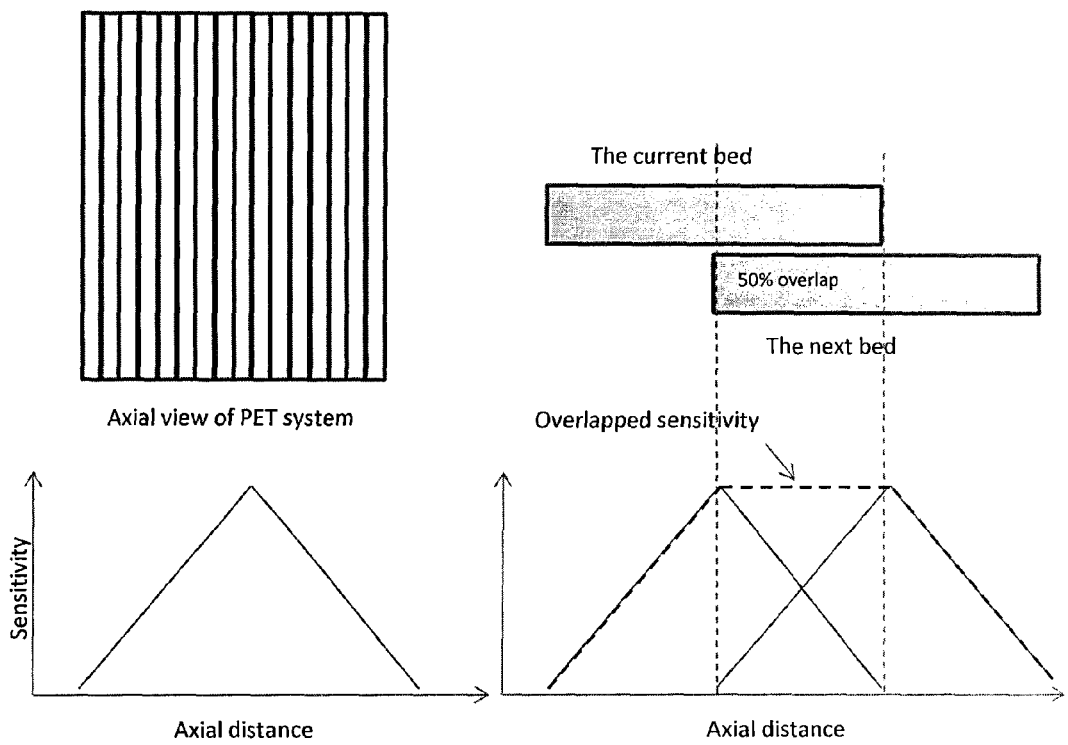
FIG. 2(A) illustrates an axial view of PET scanning system 10 including a plurality of PET rings 20 and a relationship between axial sensitivity of PET scanning system 10 and an axial distance of PET ring 20.
FIG. 2(B) illustrates bed positions having an overlap of 50% as bed 30 moves in a bed movement direction through PET scanning system 10 and a relationship between overlapped sensitivity of PET scanning system 10 and an axial distance of PET ring 20.

FIG. 2(A) illustrates an axial view of PET scanning system 10 including a plurality of PET ring 20 and a relationship between axial sensitivity of PET scanning system 10 and an axial distance of PET ring 20.

As illustrated in FIG. 2(A), axial sensitivity of PET scanning system 10 is greater towards the middle of the plurality of PET ring 20 and axial sensitivity linearly decreases away from the middle and towards either end of the plurality of PET ring 20. As a result, uniform axial sensitivity of scan data can be obtained by overlapping scans taken at adjacent bed positions, as illustrated in FIG. 2(B).

FIG. 2(B) illustrates bed positions having an overlap of 50% as bed 30 moves in the bed movement direction through PET scanning system 10. Scan data is collected at each bed position by PET scanning system 10 of the scan target, a patient, upon bed 30 as bed 30 moves through PET scanning system 10. Because the bed positions overlap, sensitivity of PET scanning system 10 is increased. FIG. 2(B) illustrates a relationship between an overlapped sensitivity of PET scanning system 10 and an axial distance of PET ring 20. In FIG. 2(B), axial sensitivity is increased at positions closer to an edge of the plurality of PET ring 20 by acquiring scan data at overlapping adjacent bed positions. While FIG. 2(B) illustrates bed positions having an overlap of 50%, PET scanning system 10 can operate with an overlap of bed positions with a value anywhere between 0% and 100%.

While sensitivity is increased as the amount of bed position overlap increases, scan speed decreases as the amount of bed position overlap increases. Alternatively, scan speed is increased when an amount of bed position overlap decreases.

After scan data is collected by PET scanning system 10, PET scanning system 10 processes the collected scan data to identify scatter events. Because bed positions overlap, much of the scan data collected by PET scanning system 10 can be duplicative. In other words, calculation of scatter data at each bed position can be unnecessary because the scan data collected from a first bed position is the same as scan data collected at a second bed position that overlaps with the first bed position. As a result, PET scanning system 10 performs method 100 illustrated in FIG. 3 to decrease the computational time in the scatter estimation, but keep the similar image quality by utilizing the overlaps between adjacent bed positions.

Figure 3:
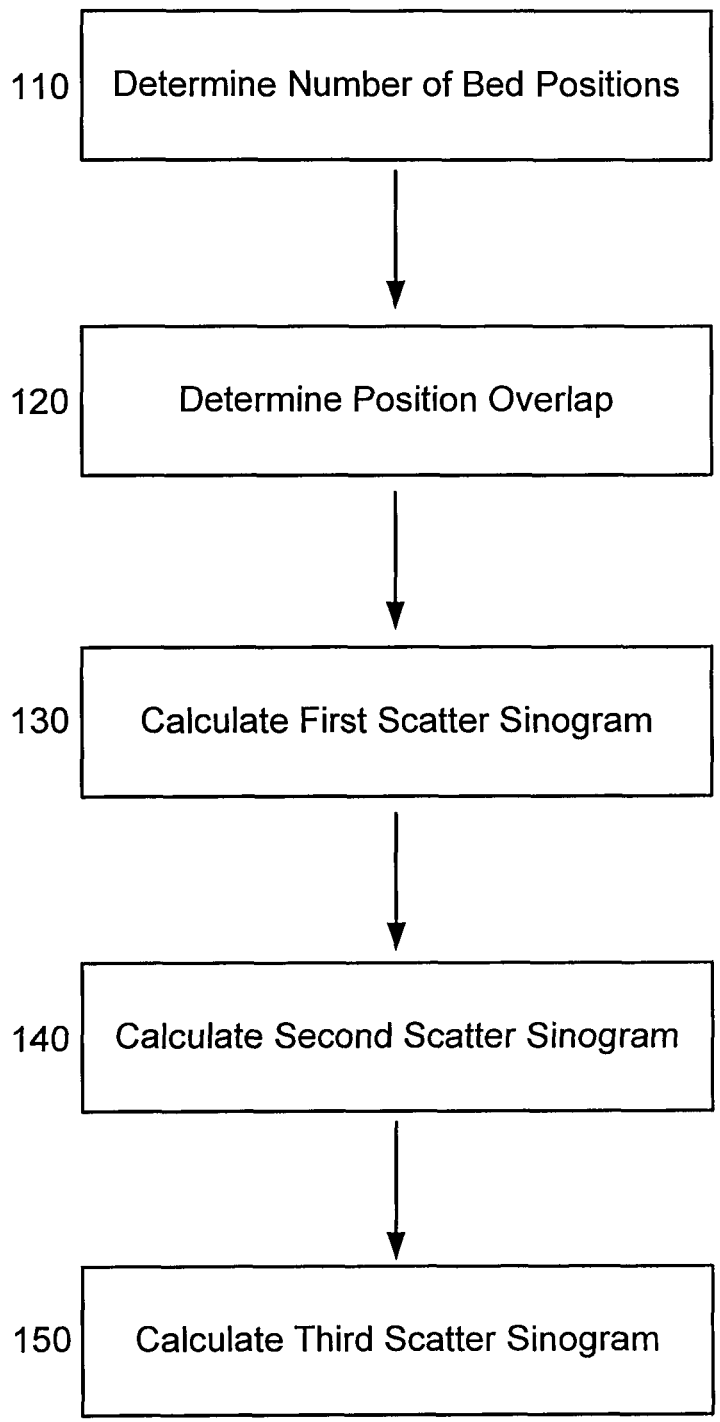
FIG. 3 illustrates method 100 for estimating scatter in accordance with a plurality of bed positions.
Figure 4:
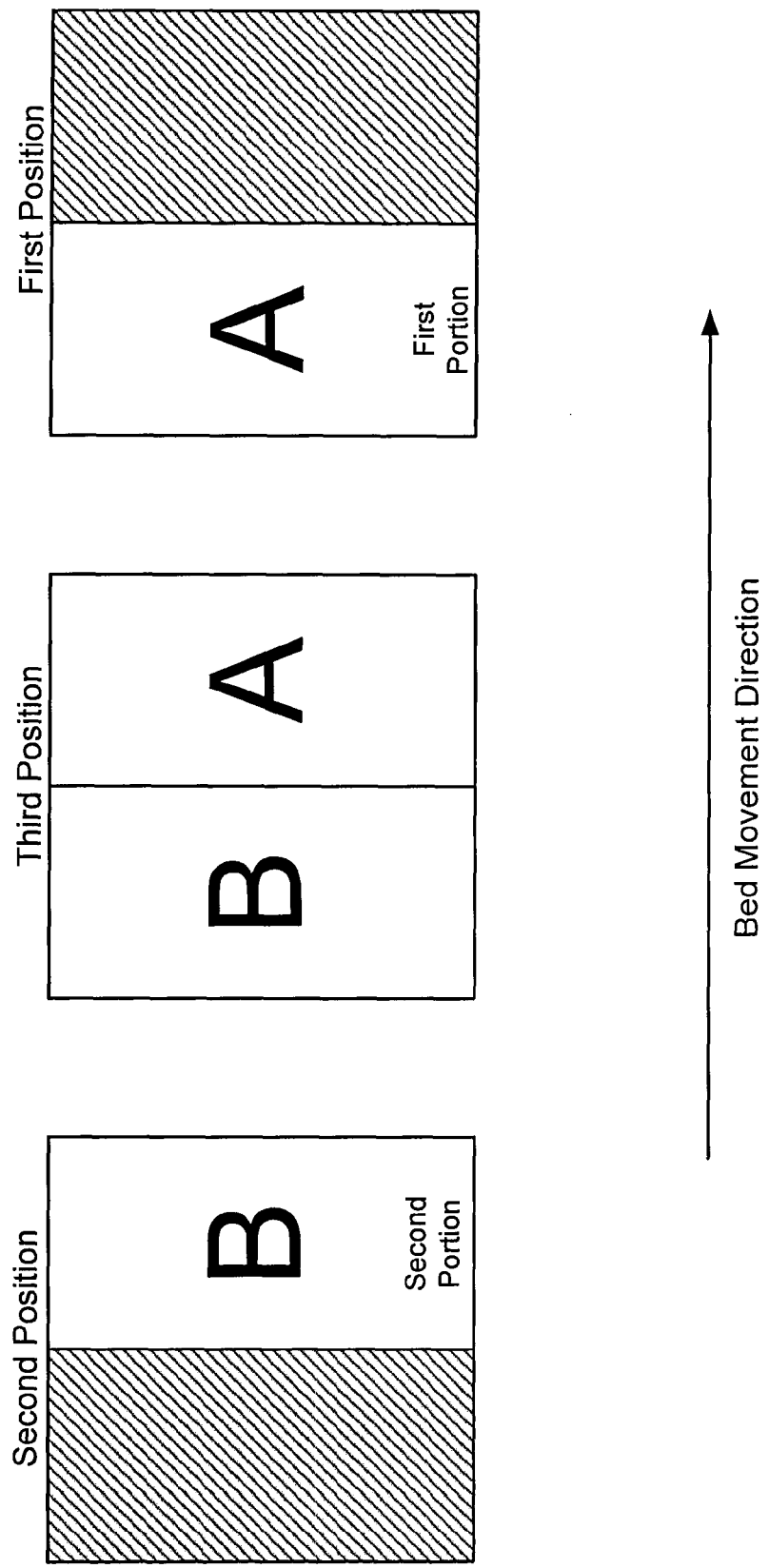
FIG. 4 illustrates bed positions of bed 30 as moves through PET scanning system 10 in the bed movement direction.

FIGS. 3 and 4 will be referenced to describe method 100 performed by PET scanning system 10. In particular, FIG. 3 illustrates method 100 for estimating scatter in accordance with a plurality of bed positions. FIG. 4 illustrates bed positions of bed 30 as bed 30 moves through PET scanning system 10 in the bed movement direction.

Bed 30 moves through PET scanning system 10 in the bed movement direction illustrated in FIG. 1(A). Prior to performance of method 100, scan data is collected by PET ring 20 as bed 30 moves through PET scanning system 10. Alternatively, method 100 is performed by PET scanning system 10 on scan data stored in a memory, e.g., data that has been previously collected.

In method 100, PET scanning system 10 performs method 100 by beginning at Step 110.

In Step 110, PET scanning system 10 determines a number of bed positions. In exemplary implementations, the number of bed positions is a preset amount. Alternatively, the number of bed positions is adjusted according to a desired sensitivity or scanning speed. Further, the number of bed positions can be input or set by a user. After determining the number of bed positions, PET scanning system 10 proceeds to Step 120.

In Step 120, PET scanning system 10 determines an amount of overlap between each bed position. In exemplary implementations, the amount of overlap between adjacent bed positions is a preset amount. Alternatively, the amount of overlap between adjacent bed positions can depend upon any of the number of bed positions, a length of bed 30, and a size of a scanning area of each bed position. Further, the amount of overlap can be input or set by a user. After determining the amount of overlap, PET scanning system proceeds to Step 130.

In Step 130, PET scanning system 10 calculates a first scatter sinogram. In an exemplary implementation, PET scanning system 10 calculates the first scatter sinogram by processing the scan data collected at the first bed position illustrated in FIG. 4. Then in Step 140, PET scanning system 10 calculates a second scatter sinogram by processing the scan data collected at the second bed position illustrated in FIG. 4. The scan data collected within the first bed position is used to calculate the first scatter sinogram and the scan data collected within the second bed position is used to calculate the second scatter sinogram.

In Step 150, PET scanning system 10 derives a third scatter sinogram. In Step 150, PET scanning system 10 does not derive the third scatter sinogram by processing the scan data collected at a third bed position. Instead, PET scanning system 10 derives a third scatter sinogram for the third position based on the first scatter sinogram and the second scatter sinogram.

In the exemplary implementation as illustrated in FIG. 4, the first bed position has a first amount of overlap of 50% with the third bed position and the second bed position has a second amount of overlap of 50% with the third bed position. Because of the respective overlaps of the first, second and third bed positions, the scatter data collected in the third bed position can be substantially the same as scatter data collected in a portion of the first bed position and in a portion of the second bed position.

As illustrated in FIG. 4, the third scatter sinogram is derived by PET scanning system 10 in Step 150 by copying portion A of the first scatter sinogram calculated from scatter data collected at the first bed position, and copying portion B of the second scatter sinogram calculated from scatter data collected at the second bed position. Thus, PET scanning system 10 derives the third scatter sinogram in Step 150 by copying portion A of the first scatter sinogram and copying portion B of the second scatter sinogram.

Note that error in the derived scatter sinograms increases with a decrease of an amount of overlap between adjacent bed positions. Further detail of the derivation of the third scatter sinogram in Step 150 is described below.

Returning to the method illustrated in FIG. 3, PET scanning system 10 calculates scatter sinograms for scan data collected at ends of bed 30. Such calculations can be necessary because bed positions at ends of bed 30 are only adjacent to one other bed position. In other words, scatter sinograms are calculated for scatter data at an end bed position because there is not enough overlapping data for the derivation of a scatter sinogram. For example, in a PET scan acquisition with 8 bed positions and an amount of overlap of 50%, sinograms at bed positions 1, 3, 5, 7 and 8 is calculated. For bed positions 2, 4 and 6, however, scatter sinograms is derived from the scatter sinograms calculated at neighboring bed positions. For example, the scatter sinogram for the scatter data collected at bed position 2 is derived from the scatter sinograms calculated for scatter data collected at bed positions 1 and 3.

By deriving scatter sinograms for scan data at bed positions that are overlapped by adjacent bed positions, i.e., skipping calculations of scatter sinograms, computation time can be saved as shown below:

$$\text{Time saved} = \left(1 - \frac{\left\lfloor \frac{n}{N_s + 1} \right\rfloor + m}{n}\right) \times 100\%$$

$$N_s = \begin{cases} 1 & x < 0.5 \\ \text{ROUND}\left(\frac{x}{1-x}\right) & x \geq 0.5 \end{cases}$$

$$m = \begin{cases} 1, & n \% (N_s + 1) \leq 1 \\ 2, & n \% (N_s + 1) > 1 \end{cases}$$

where n is the total number of bed positions, x is the overlap region in the axial direction, and Ns is the number of bed positions to skip. For example, an amount of overlap of 50% can yield a 1-bed position skip, an amount of overlap of 66.7% can yield a 2-bed position skip, and an amount of overlap of 75% can yield a 3-bed position skip.

Note that PET scanning system 10 rescales the scatter sinograms from the previous bed position and the next bed position when an overlap amount is greater than 50%. Further, PET scanning system 10 can perform a tail-fitting process on derived scatter sinograms to rescale them to the current bed position. Additionally, PET scanning system 10 interpolates scatter data for missing slices in scatter sinograms when an amount of overlap between adjacent bed positions is less than 50%. Further detail of these processes is provided below.

Alternatively, method 100 as illustrated in FIG. 3 is performed by processing circuitry. In other words, method 100 is performed by processing circuitry upon data stored in a memory. Further, computer executable instructions for the steps described in method 100 are stored in a memory and executed by the processing circuitry. For example, a non-transitory computer readable medium stores computer executable instructions that, when executed by the processing circuitry, causes the processing circuitry to perform the method as illustrated in FIG. 3.

Figure 5:
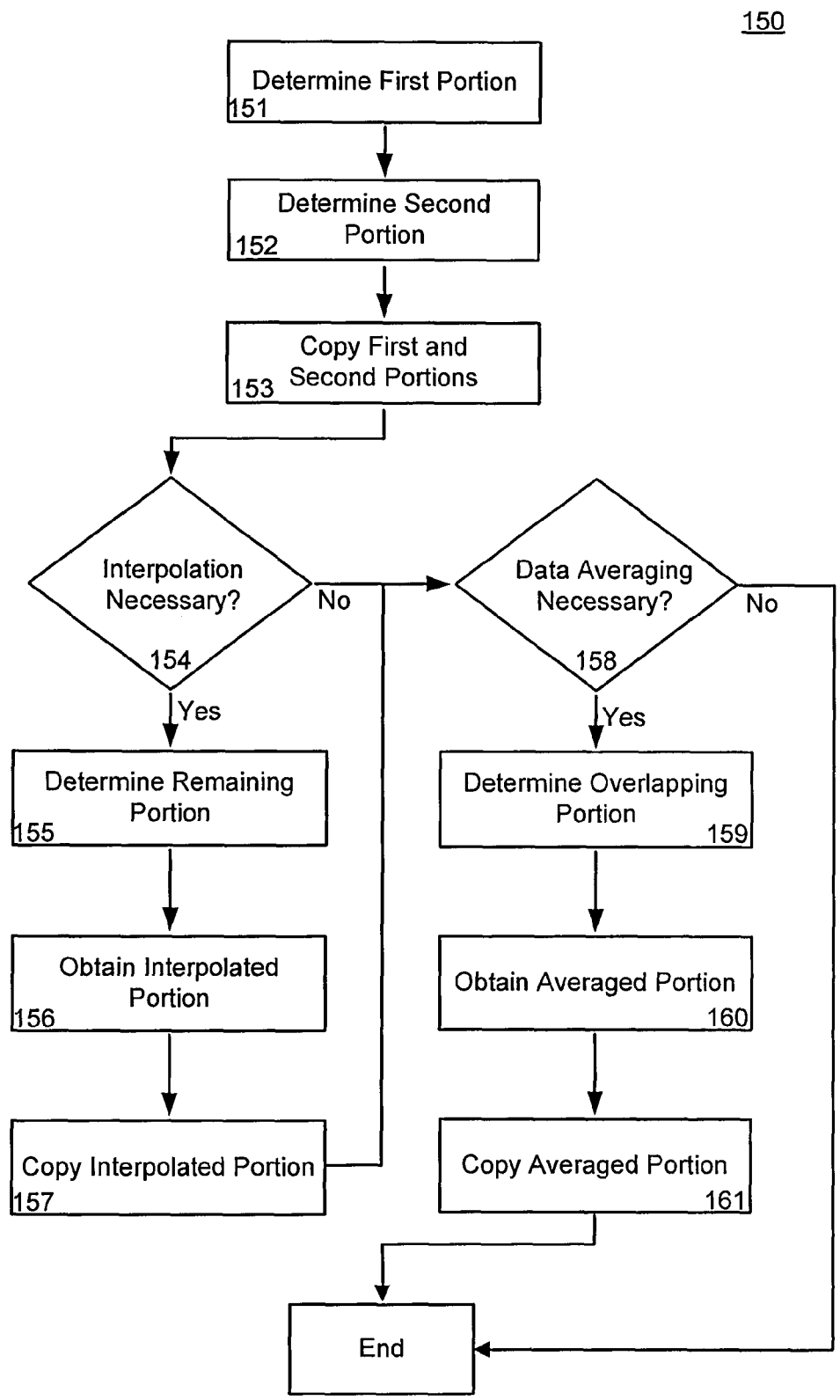
FIG. 5 provides details of steps performed in Step 150 of method 100.

FIG. 5 provides details of steps performed in Step 150 of method 100.

In Step 151, PET scanning system 10 determines a first portion of the first scatter sinogram. In the exemplary implementation illustrated in FIG. 4, the first portion of the first scatter sinogram is labeled portion A. PET scanning system 10 determines the first portion of the first scatter sinogram according to (i) the amount of overlap of the bed positions, as determined in Step 120, (ii) the portion of the first bed position that overlaps with the third bed position, and (iii) an angle θ of LORs within the first bed position. Angle θ of LORs will be discussed below with reference to FIGS. 7(A)-7(C).

For example, when the amount of overlap is determined in Step 120 to be 50%, and θ=0, then in Step 151, PET scanning system 10 determines that the first portion is equal to the 50% of the first scatter sinogram that overlaps with the third bed position.

In Step 152, PET scanning system 10 determines a second portion of the second scatter sinogram. In the exemplary implementation illustrated in FIG. 4, the second portion of the second scatter sinogram is labeled portion B. PET scanning system 10 determines the second portion of the second scatter sinogram according to (i) the amount of overlap of the bed positions, as determined in Step 120, (ii) the portion of the second bed position that overlaps with the third bed position, and (iii) angle θ of LORs within the second bed position.

For example, when the amount of overlap is determined in Step 120 to be 40% and θ=0, then in Step 152, PET scanning system 10 determines that the second portion is equal to the 40% of the second scatter sinogram that overlaps with the third bed position.

In Step 153, PET scanning system 10 copies the first portion and second portion to create a third scatter sinogram. In particular, PET scanning system 10 copies the first portion to the third scatter sinogram in which the third position overlaps with the first position, from which the first portion was created. PET scanning system 10 copies the second portion to the third scatter sinogram in which the third position overlaps with the second position, from which the second portion was created. In other words, PET scanning system 10 creates the third scatter sinogram consistent the overlapping adjacent bed positions.

In Step 154, PET scanning system 10 determines whether interpolation is necessary to complete the third sinogram. Interpolation may be necessary, for example, when θ≠0° or when an amount of overlap is less than 50%. For example, when an amount of overlap of bed positions is 50% and θ≠0°, interpolation may be necessary to compute a remaining portion of the third sinogram. If PET scanning system 10 determines that interpolation is necessary, PET scanning system 10 proceeds to Step 155. Should PET scanning system 10 determine that interpolation is not necessary, PET scanning system 10 proceeds to Step 158.

In Step 155, PET scanning system 10 determines a remaining portion that is necessary to complete the third scatter sinogram. For example, when the amount of overlap is less than 50%, each of the first portion and the second portion copied from the first and second scatter sinograms are less than 50%, thus leaving a third sinogram less than 100% complete. Should θ≠0°, interpolation may also be necessary. Further discussion of θ and interpolation will be provided below with reference to FIGS. 7(A)-7(C).

In other words, PET scanning system 10 determines a remaining portion of the third scatter sinogram based on a difference between 100% and a combination of the first portion and the second portion.

Once the remaining portion is determined, PET scanning system 10 proceeds to Step 156. In Step 156, PET scanning system 10 interpolates the remaining portion to create an interpolated portion. The interpolation process performed by PET scanning system 10 is described in detail below.

In Step 157, PET scanning system 10 copies the interpolated portion into the third scatter sinogram. In particular, PET scanning system 10 copies the interpolated portion in between the first portion and the second portion. In other words, the interpolated portion represents a calculated transition between the first portion and the second portion. PET scanning system 10 then proceeds to Step 158.

After completion of Step 157, or when PET scanning system 10 determines that interpolation is not necessary in Step 154, PET scanning system 10 proceeds to Step 158. In Step 158, PET scanning system 10 determines whether data averaging is necessary. Data averaging may be necessary, for example, when an amount of overlap is greater than 50%, depending upon a value of θ. Should PET scanning system 10 determine that data averaging is necessary, PET scanning system 10 proceeds to Step 159. However, should PET scanning system 10 determine that data averaging is not necessary, method Step 150 is complete.

In Step 159, PET scanning system 10 determines an overlapping portion of the first portion and the second portion. In other words, because the amount of overlap is greater than 50%, the overlapping portion is a segment in which the first portion and the second portion overlap. In an exemplary implementation, the overlapping portion includes a first part of the first portion that overlaps with a second part of the second portion.

As a result, PET scanning system 10 determines an overlapping portion of the third scatter sinogram based on a difference between 100% and a combination of the amount of overlap of the first scatter sinogram and the amount of overlap of the second scatter sinogram. In an exemplary embodiment, should PET scanning system 10 determine an interpolation portion in Step 157, the overlapping portion determined by PET scanning system 10 in Step 159 could coincide with at least a part of the interpolation portion.

Once the overlapping portion is determined, PET scanning system 10 proceeds to Step 160. In Step 160, PET scanning system 10 rescales the overlapping portion of the first portion and the second portion by averaging or weighting the overlapping portion to create an averaged portion. The rescaling process performed by PET scanning system 10 is described in detail below.

Finally, in Step 161, PET scanning system 10 copies the averaged portion into the third scatter sinogram to replace the overlapping portions of the first portion and the second portion. In particular, PET scanning system 10 copies the averaged portion between the remainder of the first portion and the second portion.

The copying and/or interpolating portions of scatter sinograms within method 100 is achieved by PET scanning system 10 by the copying and/or interpolating LORs of captured scan data of the respective adjacent bed position. Further discussion of copying and interpolating LORs is provided below.

Discussion will now transition to estimating scatter using the MBSE method.

Statistically, LORs in different bed positions include a same number of scatter events because they pass through a same object at a same position. In other words, a same scatter event is detected by detectors 22 in different PET ring 20. When detected by detectors 22 in different PET ring 20, the scatter event is detected in different LORs.

Duplicate computation for scatter estimation occurs in a bed position that is covered by multiple bed position data acquisition. In other words, duplicate computation for scatter estimation occurs when bed positions overlap. As a result, scatter estimation for overlapping bed positions are accurately estimated from adjacent bed positions for LORs with small axial tilted angles.

The MBSE method can be performed in the raw sinogram domain or in the interpolated sinogram domain. A raw sinogram includes all possible LORs in a corresponding FOV. For example, there can be numRadial×numPhi×numRing×numRing LORs in a specific FOV raw sinogram. Those LORs can be used directly in the final reconstruction.

However, it can be difficult to calculate such a huge number of LORs using the MBSE method even with interpolation processes. Thus, it is beneficial to estimate scatter sinograms in the interpolated sinogram domain instead of in the raw sinogram domain. This is because the interpolated sinogram domain has much fewer LORs than the raw sinogram domain. For example, there can be only $N_s \times N_\phi \times N_z * N_\theta$ LORs in a specific FOV interpolated sinogram, where the total number of LORs is much fewer than that in a raw sinogram ($N_s, N_\phi, N_z$ and $N_\theta$ are the number of s, $\phi$, z and $\theta$). After calculating scatter interpolated sinograms, a back-interpolation process is needed to transfer scatter events back to the raw sinograms for the final reconstruction.

Figure 6A:
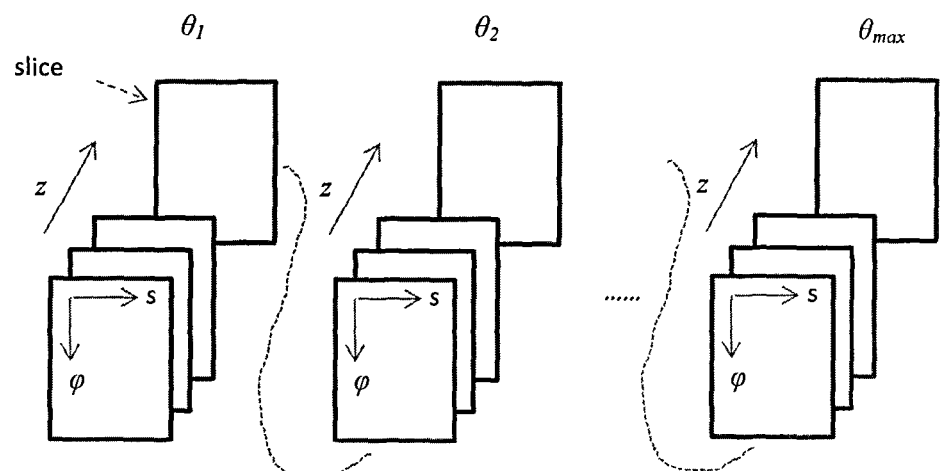
FIG. 6(A) illustrates an interpolated sinogram.
Figure 6B:
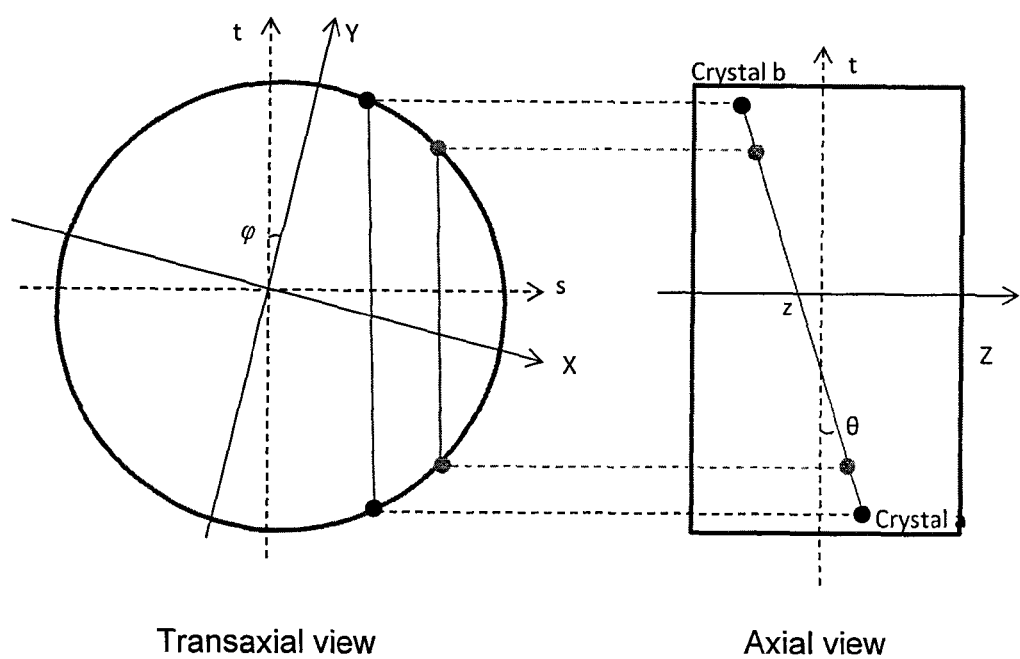
FIG. 6(B) illustrates the coordinate system of an interpolated sinogram in a transaxial view (left) and an axial view (right)

FIGS. 6(A) and 6(B) illustrate an interpolated sinogram and its coordinate system in transaxial and axial views.

In an interpolated sinogram domain, any LOR is represented by a set of parameters (s, $\phi$, z, $\theta$) and a typical interpolated sinogram is arranged with s varying fastest and $\theta$ varying slowest, as illustrated in FIG. 6(A). In particular, z and $\theta$ are calculated as follows:

$$z = (z_a + z_b)/2$$

$$\theta = \tan^{-1} \frac{z_b - z_a}{\sqrt{(x_b - x_a)^2 + (y_b - y_a)^2}}$$

In an exemplary implementation, the last three parameters are fixed. However, s can vary with each FOV.

FIG. 6(B) illustrates the coordinate system of an interpolated sinogram. In particular, FIG. 6(B) illustrates a set of LORs with fixed (z, $\theta$), but different (s, $\phi$) in an axial view. As illustrated, each LOR is superimposed together at a same line, but with different ending points. Such a same line includes two ending points that are symmetric about a middle point on the Z-axis. As a result, in each of the following figures, any line in an axial view represents a set of LORs which actually form one slice with fixed (z, $\theta$) in an interpolated sinogram.

Figure 7A:
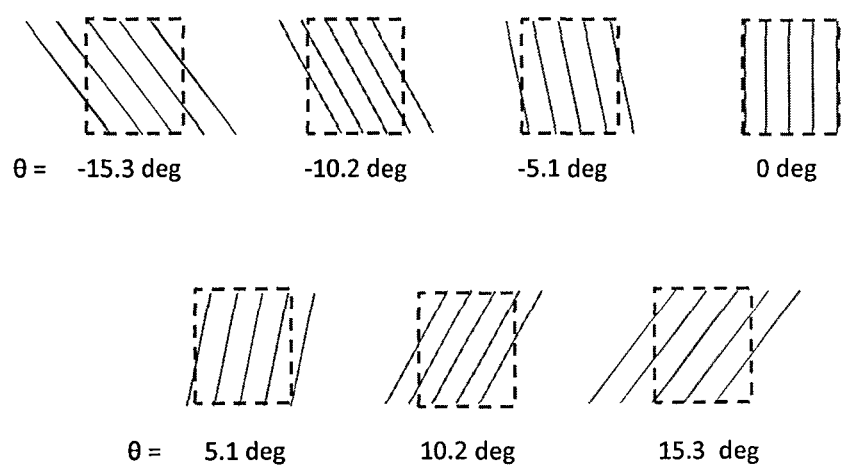
FIG. 7(A) illustrates lines of response (LORs) of an interpolated sinogram of 700-mm-FOV and an amount of overlap of 50% with varying θ's ranging from −15.3 to 15.3 degrees.

FIGS. 7(A)-7(C) illustrate LORs for different $\theta$'s when an amount of overlap of adjacent bed positions is 50%.

PET scanning system 10 determines whether a LOR can be directly copied from an adjacent bed position or whether a LOR requires interpolation. PET scanning system 10 makes such a determination by analyzing tilted angle $\theta$ and the z coordinate. In particular, PET scanning system 10 utilizes the following equation that relates a LOR in a current bed position (third position) to LORs in previous bed position (second position) and/or next bed position (first position):

$$LOR^c(s,\phi,z,\theta) = LOR^p(s,\phi,z-z_{shift},\theta) = LOR^n(s,\phi,z+z_{shift},\theta)$$

Where p represents a previous bed position, c represents a current bed position and n represents a next bed position. Additionally, $z_{shift} = \text{overlap }\% * z_{max}$ and $0 \leq z \pm z_{shift} \leq z_{max}$, where $z_{max}$ is the PET scanner' axial field-of-view. The indexing of $+z_{shift}$ or $-z_{shift}$ in previous and next bed depends on the increment direction of the z-axis.

In other words, PET scanning system 10 can directly copy a LOR from an adjacent bed position when $LOR^p$ and/or $LOR^n$ are available for creation of a scatter sinogram. However, when both $LOR^p$ and $LOR^n$ are not available, PET scanning system 10 must perform an interpolation process with $LOR^p$ and/or $LOR^n$ to calculate $LOR^c$ for the creation of the scatter sinogram.

In an exemplary implementation with an interpolated sinogram of 700-mm-FOV and an amount of overlap of 50%, the scatter interpolated sinogram have 7$\theta$'s ranging from −15.3 to 15.3 degrees and 95 z's covering the whole axial FOV, e.g., 48 rings. FIG. 7(A) illustrates each $\theta$, which includes a set of LORs with different z's are grouped together. FIG. 7(B) illustrates 4 different $\theta$'s with an amount of overlap of 50%. In FIG. 7(B), solid lines stand for a set of LORs which can be directly copied from either previous or next bed while dashed lines stand for a set of LORs which can be partially copied or partially interpolated from either previous or next bed position. Other $\theta$'s with positive values are symmetric with ones with negative values and therefore are not illustrated in FIGS. 7(A)-7(C). Boundary LORs are indicated by ① and ② in FIGS. 7(B) and 7(C), and any LORs between them can require interpolations.

As illustrated in FIG. 7(C), for any LORs between LOR ① and ②:

Crystal a and b can be one of three cases:
(1) a and b all locate in the previous bed, such as a triangle;
(2) a and b all locate in the next bed, such as an 'x'; and
(3) a and b locate in the previous and next bed, such as a square.

Only LORs of case 3 are interpolated from their existing neighboring LORs.

Figure 8:
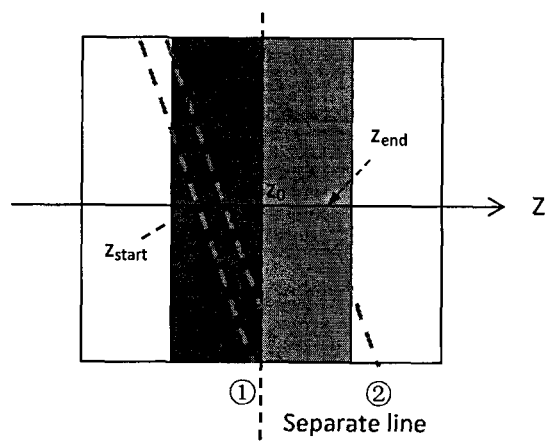
FIG. 8 illustrates a calculation percentage of copied LORs in an overlapping bed position.

FIG. 8 illustrates a calculation percentage of copied LORs in a dashed line.

In an exemplary embodiment, PET scanning system 10 uses known properties of interpolated sinograms to calculate the percentage of copied LORs:
(1) Two crystals of a LOR have opposite t coordinates, i.e., $t_a + t_b = 0$ (its two ending points are symmetric about its middle point); and
(2) Crystals of a set of LORs uniformly distributed along the line in an axial view since s and $\phi$ are uniformly sampled.

Therefore, the percentage of copied LORs in a dashed line is calculated by the line segment (2*L) divided by the length of whole dashed line, as shown in FIG. 8.

Calculations of copy % are strongly related to the scanning geometry of PET scanning system 10. However, such calculations of copy % may be approximated as in the following discussion.

In an exemplary embodiment, then, PET scanning system 10 derives the formula to calculate this percentage by:

$$\text{copy}_{dashed\text{-}line}(z, \theta) \% = \frac{\text{copied } LORs \text{ in a dashed line}}{\text{total } LORs \text{ in a dashed line}} \times 100\%$$

$$= \frac{2 \times L}{\text{length of a dashed line}} \times 100\%$$

$$= \frac{2 \times \frac{|z_0 - z|}{\sin\theta}}{\frac{transFOV}{\cos\theta}} \times 100\%$$

$$= \frac{2 \times |z_0 - z|}{transFOV \tan\theta} \times 100\%$$

In an interpolated sinogram, both transaxial FOV and axial FOV can be considered. Any LORs out of axial FOV, i.e., $z_a$ and/or $z_b < 0$ or $z_a$ and/or $z_b > z_{max}$, are not included in the sinogram. For example, any LORs outside of the dashed boxes in FIG. 7(A) are partially or totally discarded depending on locations of their ending points. To simplify the calculation, PET scanning system 10 first calculates copy($\theta$)% without considering restriction of axial FOV, then introduces an additional parameter eff($\theta$) to take care of axial FOV.

Firstly, without considering axial FOV, PET scanning system 10 calculates copy($\theta$)% for a given tilted angle $\theta$ as:

$$\text{copy}(\theta) \% = \frac{\text{copied } LORs \text{ in } \theta}{\text{total } LORs \text{ in } \theta} \times 100\%$$

$$= \frac{\text{copied } LORs \text{ from solid lines} + \text{copied } LORs \text{ from dashed lines}}{\text{total } LORs \text{ in } \theta} \times 100\%$$

$$= \frac{N_s \times N_\varphi \times (z_{max} - (z_{end} - z_{start})) + N_s \times N_\varphi \times \sum_{z=z_{start}}^{z=z_{end}} \text{copy}_{dashed\text{-}line}(z, \theta) \%}{N_s \times N_\varphi \times N_z} \times 100\%$$

$$= \frac{(z_{max} - (z_{end} - z_{start})) + \sum_{z=z_{start}}^{z=z_{end}} \text{copy}_{dashed\text{-}line}(z, \theta) \%}{N_z} \times 100\%$$

Where $z_{end}$ ($z_{start} = -z_{end}$) is given by:

$$z_{end} = transFOV \tan\theta/2$$

And $N_s$, $N_\varphi$, and $N_z$ are the number of s, $\phi$ and z.

For example, copy($\theta$)% is about 51% when $\theta = 10.2$ and transFOV = 700 mm.

Then the total copy % is given by:

$$\text{total copy } \% = \frac{1}{N_\theta} \sum_{\theta=\theta_{min}}^{\theta=\theta_{max}} \text{copy}(\theta) \%$$

In an exemplary implementation, PET scanning system 10 copies about 44% of LORs from the previous or next bed position with an amount of overlap of 50%.

After discarding any LORs out of axial FOV, copy % becomes larger since a lot of LORs are not required in scatter sinograms especially for large tilted angles. Roughly, PET scanning system 10 calculates copy % without out-of-FOV LORs by:

$$\text{total copy } \% = \frac{1}{\sum_{\theta=\theta_{min}}^{\theta=\theta_{max}} eff(\theta)} \sum_{\theta=\theta_{min}}^{\theta=\theta_{max}} eff(\theta) * \text{copy}(\theta) \%$$

Where eff($\theta$) is the effective LORs rate (=LORs in axial FOV/all LORs).

For a 700-mm-FOV, eff($\theta$) is about 1.4%, 25%, 63%, and 100% for $\theta = \pm 15.3, \pm 10.2, \pm 5.1$, and 0 degree. As a result, PET scanning system 10 achieves a final copy % of approximately 80% for an amount of overlap of 50%.

Figure 9A:
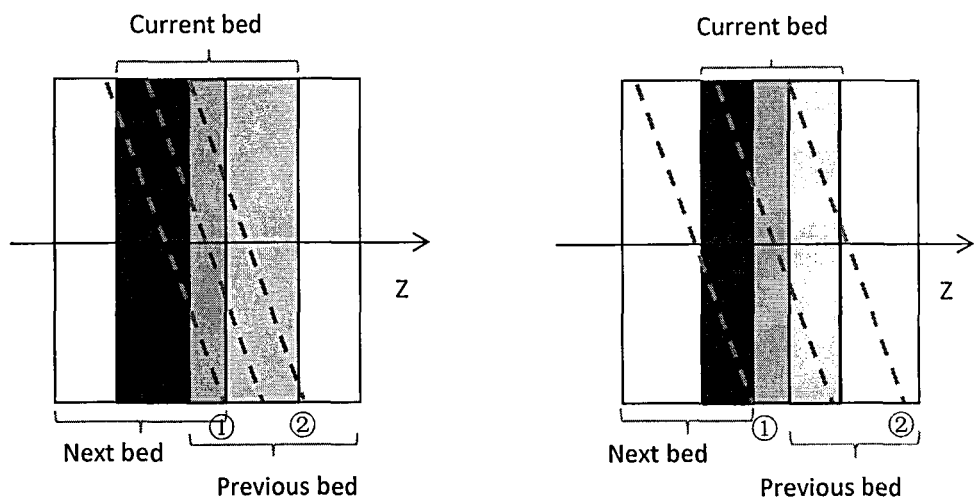
FIG. 9(A) illustrates adjacent bed positions when an amount of overlap is greater than 50% (left) and when an amount of overlap is less than 50% (right)

FIG. 9(A) illustrates adjacent bed positions when an amount of overlap is greater than 50% (left) and when an amount of overlap is less than 50% (right).

When an amount of overlap of adjacent bed positions is greater than 50%, as illustrated on the left side of FIG. 9(A), the copy % becomes larger and the error of the method performed by PET scanning system 10 further decreases. On the other hand, when an amount of overlap of adjacent bed positions is less than 50%, as illustrated on the right side of FIG. 9(A), the copy % becomes smaller and the error of this method increases.

When an amount of overlap is greater than or equal 50%, as illustrated on the left side of FIG. 9(A), LORs in the current bed position can be directly copied from the previous or next bed position should they be available. When an amount overlap is greater than 50%, there can be more than one available LOR from the previous or next bed positions for a target LOR in the current bed position. That is, when the amount of overlap is greater than 50%, PET scanning system 10 can geometrically average the two or more LORs to get a target LOR. Alternatively, PET scanning system 10 can use a weight function w(z) that is proportional to the axial sensitivity of PET scanning system 10 to calculate the target LOR:

$$\text{Target } LOR = \frac{\sum_{i=1}^{n} LOR_i \text{ from neighboring beds} * w(z_i)}{\sum_{i=1}^{n} w(z_i)}$$

Figure 9B:
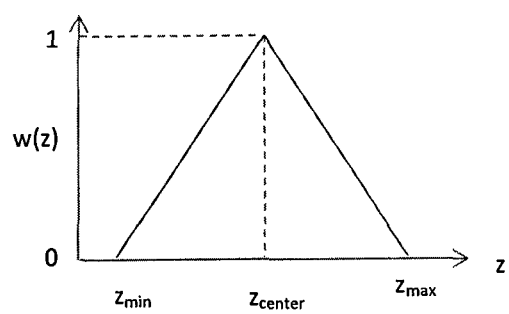
FIG. 9(B) illustrates a weight function w(z) for weighting same LORs from different bed positions.

FIG. 9(B) illustrates a weight function w(z) for weighting same LORs from different bed positions.

Alternatively, when an amount of overlap is less than 50%, as illustrated on the right side of FIG. 9(A), LORs in the current bed position can be interpolated from scan data in overlapping adjacent bed positions. When corresponding $LOR^p$ and $LOR^n$ are not available, then $LOR^c$ can be interpolated from neighbors of $LOR^p$ and/or $LOR^n$. PET scanning system 10 can use any kind of interpolation methods such as nearest neighbors, linear with different orders in each dimension, cubic and splines to acquire the desired $LOR^c$ based on the closest neighbors of $LOR^p$ and/or $LOR^n$. In particular, $LOR^c(s,\phi,z,\theta) = f(LOR^p(s+\Delta s, \phi+\Delta\phi, z-z_{shift}+\Delta z, \theta+\Delta\theta),$
$LOR^n(s+\Delta s, \phi+\Delta\phi, z+z_{shift}+\Delta z, \theta+\Delta\theta))$ Where $\Delta s$, $\Delta \phi$, $\Delta z$ and $\Delta \theta$ stand for changes as small as possible (therefore, closest neighbors). Depending on the accuracy and computational requirements, the method of interpolation and the number of neighbors can be varied.

The method for estimating scatter performed by PET scanning system 10 can also be performed using data in the raw sinogram domain. In such calculations, the parameter set (s, $\phi$, z, $\theta$) can be replaced with (rad, phi, ringSum, ringDiff). Corresponding parameters can have similar meanings and intrinsic correlations. To understand the raw sinograms, PET scanning system 10 can simply use (rad, phi, ringSum, ringDiff) to replace (s, $\phi$, z, $\theta$) in above discussion. For example:

$LOR^c(rad,phi,ringSum,ringDiff) = LOR^p(rad,phi,ring-$
$Sum-ringSum_{shift}, ringDiff) = LOR^n(rad,phi,ring-$
$Sum+ringSum_{shift}, ringDiff)$ with
$ringSum_{shift}=$overlap %*#rings and
$0 \leq ringSum \pm ringSum_{shift} \leq$ #rings.

Figure 10:
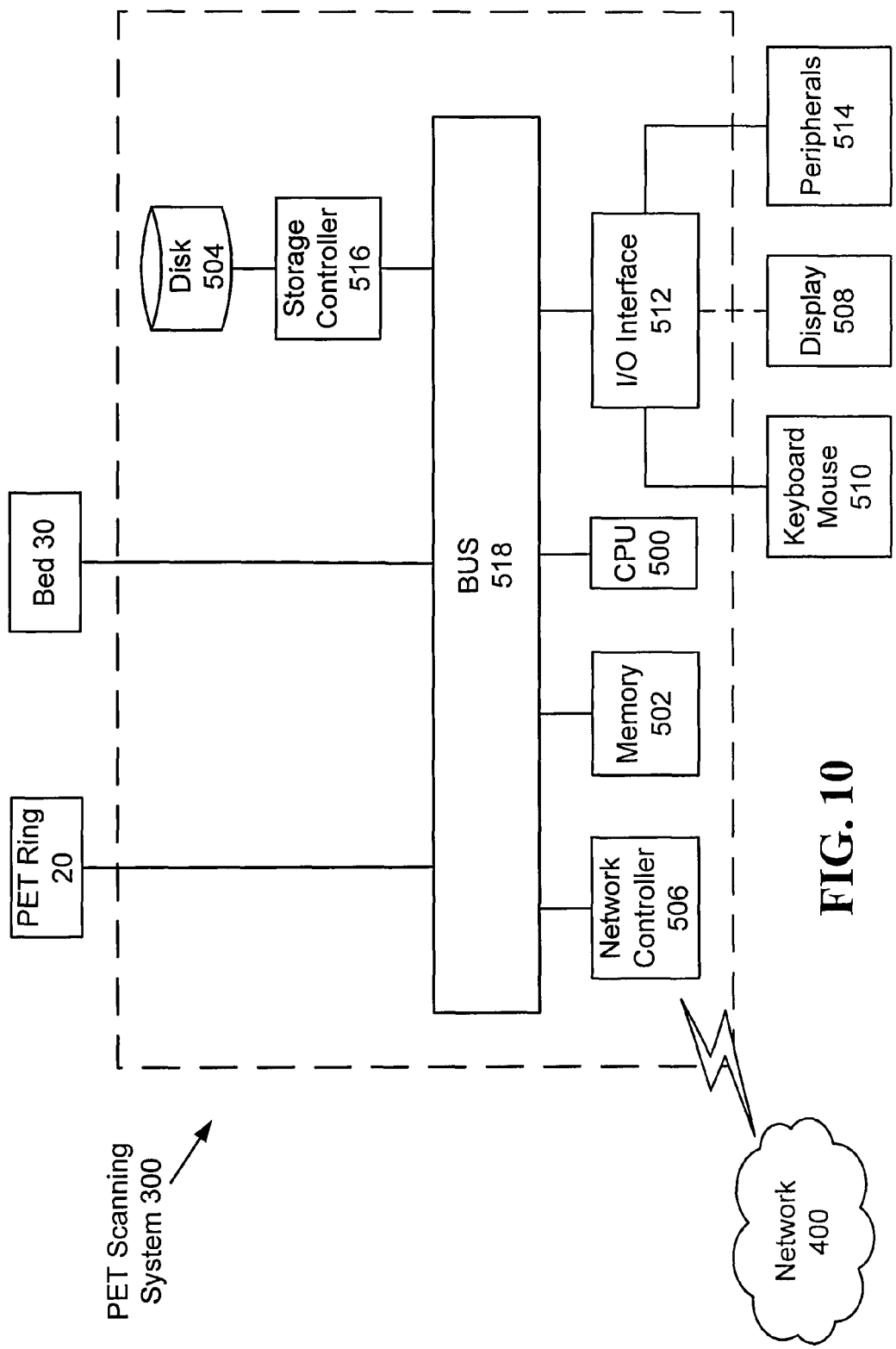
FIG. 10 illustrates an exemplary component configuration of PET scanning system 10.

FIG. 10 illustrates an exemplary component configuration of a PET scanning system. In particular, FIG. 10, PET scanning system 300 includes CPU 500, which performs the processes shown in the flowcharts and described above. Process data and executable instructions for a method for estimating scatter, as described relating to FIG. 3, is stored in memory 502. These processes and instructions can also be stored on a storage medium disk 504 such as a hard drive (HDD) or portable storage medium or can be stored remotely. Further, the claimed advancements are not limited by the form of the computer-readable media on which the instructions of the inventive process are stored. For example, the instructions can be stored on CDs, DVDs, in FLASH memory, RAM, ROM, PROM, EPROM, EEPROM, hard disk or any other information processing device with which the PET scanning system 10 communicates, such as a server or computer.

Further, the claimed advancements can be provided as a utility application, background daemon, or component of an operating system, or combination thereof, executing in conjunction with CPU 500 and an operating system such as, for example, Microsoft Windows 7, UNIX, Solaris, LINUX, Apple MAC-OS and other systems known to those skilled in the art.

CPU 500 can be implemented using discrete logic circuits. Further, CPU 500 can also be implemented as multiple processors cooperatively working in parallel to perform the instructions of the inventive processes described above. In other embodiments, PET scanning device may include a CPU, a GPU, or both.

PET scanning device 300 as illustrated in FIG. 10 can also include a network controller 506 for interfacing with network 400. Network 400 can be a public network, such as the Internet, or a private network such as an LAN or WAN network, or any combination thereof and can also include PSTN or ISDN sub-networks. Network 400 can be wired, such as an Ethernet network, or can be wireless such as a cellular network including EDGE, 3G and 4G wireless cellular systems. The wireless network can also be WiFi, Bluetooth, or any other wireless form of communication that is known.

In an exemplary implementation, the calculations performed in a method for estimating scatter in a PET scan at multiple bed positions can be performed entirely by PET scanning system 300. Alternatively, the calculations performed in the method can be subdivided and performed in series or in parallel by devices over network 400. For example, calculations can be performed by multiple devices in communication over network 400.

PET scanning system 300 can further include a general purpose I/O interface 512 that interfaces with a keyboard and/or mouse 510 as well a display 508. I/O interface 512 can also connects to a variety of peripherals 514 such as printers and scanners.

The general purpose storage controller 516 connects the storage medium disk 504 with communication bus 518 for interconnecting all of the components of the PET scanning system 300.

Figure 11A:
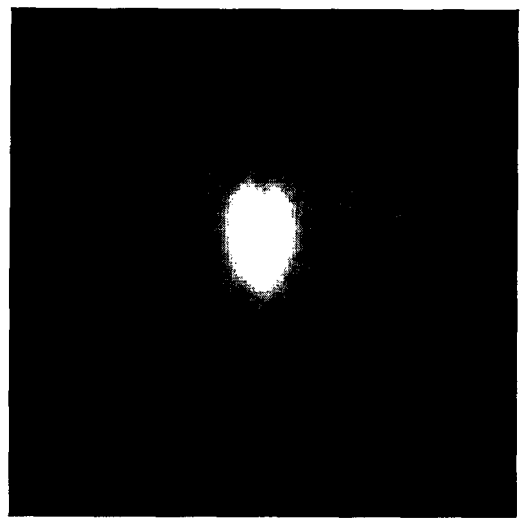
FIG. 11(A) illustrates a traversal view of a reconstructed image with scatter estimation by MBSE.
Figure 11B:
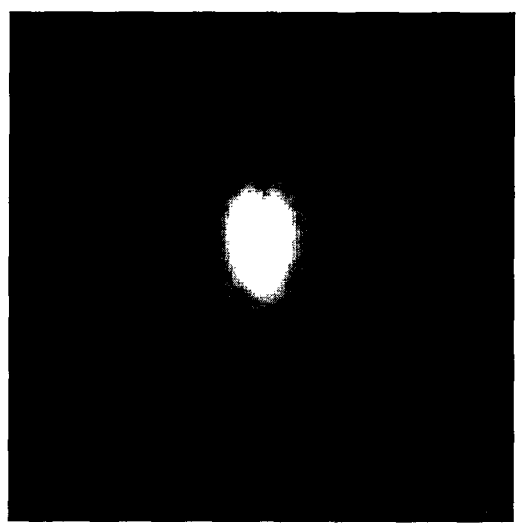
FIG. 11(B) illustrates a traversal view of a reconstructed image with scatter estimation by MBSE utilizing according to the proposed method of FIG. 3.
Figure 12A:
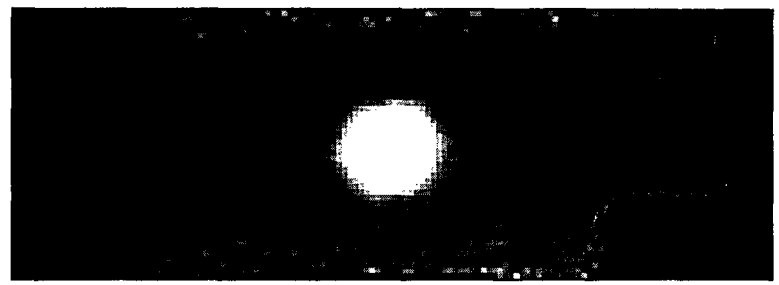
FIG. 12(A) illustrates a sagittal view of a reconstructed image with scatter estimation by MBSE.
Figure 12B:
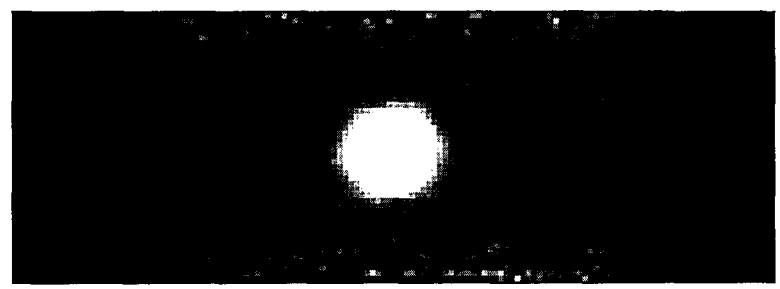
FIG. 12(B) illustrates a sagittal view of a reconstructed image with scatter estimation by MBSE utilizing according to the proposed method of FIG. 3.

FIGS. 11 and 12 illustrate reconstructed images of scanned data after scatter estimation. In particular, FIG. 11(A) illustrates a traversal view of a reconstructed image with scatter estimation by MBSE and FIG. 12(A) illustrates a coronal view of a reconstructed image with scatter estimation by MBSE. By contrast, FIG. 11(B) illustrates a traversal view of a reconstructed image with scatter estimation by MBSE utilizing according to the proposed method of FIG. 3 and FIG. 12(B) illustrates a coronal view of a reconstructed image with scatter estimation by MBSE utilizing according to the proposed method of FIG. 3.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method for estimating scatter in a positron emission tomography (PET) scan at multiple bed positions, the method comprising:
    calculating a first scatter sinogram based on scatter data obtained at a first bed position;
    calculating a second scatter sinogram based on scatter data obtained at a second bed position; and
    deriving a third scatter sinogram for a third bed position between the first bed position and the second bed position, wherein
    the third scatter sinogram is derived from the first scatter sinogram according to a first percentage of overlap of the first bed position with the third bed position, and from the second scatter sinogram according to a second percentage of overlap of the second bed position with the third bed position.

2. The method according to claim 1, wherein the step of deriving the third scatter sinogram comprises:
   determining a first portion to copy, the first portion being equal to the first percentage of the first scatter sinogram;
   determining a second portion to copy, the second portion being equal to the second percentage of the second scatter sinogram; and
   copying the first portion and the second portion to the third scatter sinogram.

3. The method according to claim 2, wherein
   the first scatter sinogram, the second scatter sinogram and the third scatter sinogram have the same dimensions as one another, and
   when a sum of the first percentage of overlap and the second percentage of overlap is less than 100%, the step of deriving the third scatter sinogram further comprises:
      determining a remaining portion of the third scatter sinogram, the remaining portion having an area that is equal to a difference between an area of the third scatter sinogram and a sum of an area of the first portion and an area of the second portion;
      interpolating the remaining portion of the third scatter sinogram to create an interpolated portion; and
      copying the interpolated portion to the third scatter sinogram, wherein the third scatter sinogram includes the first portion, the second portion, and the interpolated portion.

4. The method according to claim 2, wherein
   the first scatter sinogram, the second scatter sinogram and the third scatter sinogram have the same dimensions as one another, and
   when a sum of the first percentage of overlap and the second percentage of overlap is greater than 100%, the step of deriving the third scatter sinogram further comprises:
      determining an overlapping portion of the third scatter sinogram, the overlapping portion including a first part of the first portion that overlaps with a second part of the second portion;
      averaging the first part and the second part of the overlapping portion to create an averaged portion; and
      copying the averaged portion to the third scatter sinogram, wherein the third scatter sinogram includes the averaged portion, a first remaining part of the first portion that does not include the first part, and a second remaining part of the second portion that does not include the second part.

5. The method according to claim 2, wherein the step of copying the first portion and the second portion to the third scatter sinogram comprises:
   determining a first position for the first portion in the third scatter sinogram;
   determining a second position for the second portion in the third scatter sinogram; and
   copying the first portion to the first position and the second portion to the second position, wherein
   a size of the third scatter sinogram is equal to a size of the first scatter sinogram and equal to a size of the second scatter sinogram.

6. The method according to claim 3, wherein the step of copying the interpolated portion to the third scatter sinogram comprises:
   determining a position for the interpolated portion in the third scatter sinogram, the position of the interpolated portion being determined based on positions of the first portion and the second portion; and
   copying the interpolated portion to the position in the third scatter sinogram.

7. The method according to claim 4, wherein the step of copying the averaged portion to the third scatter sinogram comprises:
   determining a position for the averaged portion in the third scatter sinogram, the position of the averaged portion being determined based on positions of the first portion and the second portion; and
   copying the averaged portion to the position in the third scatter sinogram.

8. The method according to claim 1, wherein the first scatter sinogram and the second scatter sinogram are calculated using a model-based scatter estimation (MBSE), a background subtraction method or a convolution subtraction method.

9. The method according to claim 1, wherein the first scatter sinogram and the second scatter sinogram are calculated using Monte Carlo-based scatter estimation.

10. The method according to claim 2, wherein the step of deriving the third scatter sinogram further includes rescaling the third scatter sinogram for the third bed position.

11. The method according to claim 1, wherein the PET scan is performed with continuous bed movement.

12. The method according to claim 1, wherein the PET scan is performed using step-and-shoot bed movement.

13. The method according to claim 1, further comprising:
   determining each bed position within the multiple bed positions of the PET scan.

14. The method according to claim 1, further comprising:
   determining the first percentage of overlap; and
   determining the second percentage of overlap.

15. A non-transitory computer readable medium storing computer executable instructions that, when executed by a processor, cause the processor to perform a method for estimating scatter in a positron emission tomography (PET) scan at multiple bed positions, the method comprising, the method comprising:
   calculating a first scatter sinogram based on scatter data obtained at a first bed position;
   calculating a second scatter sinogram based on scatter data obtained at a second bed position; and
   deriving a third scatter sinogram for a third bed position between the first bed position and the second bed position, wherein
   the third scatter sinogram is derived from the first scatter sinogram according to a first percentage of overlap of the first bed position with the third bed position, and from the second scatter sinogram according to a second percentage of overlap of the second bed position with the third bed position.

16. An apparatus for estimating scatter in a positron emission tomography (PET) scan at multiple bed positions, the apparatus comprising:
   processing circuitry configured to
      calculate a first scatter sinogram based on scatter data obtained at a first bed position;
      calculate a second scatter sinogram based on scatter data obtained at a second bed position; and
      derive a third scatter sinogram for a third bed position between the first bed position and the second bed position, wherein
   the processing circuitry derives the third scatter sinogram from the first scatter sinogram according to a first percentage of overlap of the first bed position with the third bed position, and from the second scatter sinogram according to a second percentage of overlap of the second bed position with the third bed position.

17. The apparatus according to claim 16, wherein the processing circuitry is further configured to
  determine a first portion to copy, the first portion being from the first scatter sinogram;
  determine a second portion to copy, the second portion being from the second scatter sinogram; and
  copy the first portion and the second portion to the third scatter sinogram.

18. The apparatus according to claim 17, wherein
the first scatter sinogram, the second scatter sinogram and the third scatter sinogram have the same dimensions as one another, and
when a sum of the first percentage of overlap and the second percentage of overlap is less than 100%, the processing circuitry is further configured to
  determine a remaining portion of the third scatter sinogram, the remaining portion having an area that is equal to a difference between an area of the third scatter sinogram and a sum of an area of the first portion and an area of the second portion;
  interpolate the remaining portion of the third scatter sinogram to create an interpolated portion; and
  copy the interpolated portion to the third scatter sinogram, wherein the third scatter sinogram includes the first portion, the second portion, and the interpolated portion.

19. The apparatus according to claim 17, wherein
the first scatter sinogram, the second scatter sinogram and the third scatter sinogram have the same dimensions as one another, and
when a sum of the first percentage of overlap and the second percentage of overlap is greater than 100%, the processing circuitry is further configured to
  determine an overlapping portion of the third scatter sinogram, the overlapping portion including a first part of the first portion that overlaps with a second part of the second portion;
  average the first part and the second part of the overlapping portion to create an averaged portion; and
  copy the averaged portion to the third scatter sinogram, wherein the third scatter sinogram includes the averaged portion, a first remaining part of the first portion that does not include the first part, and a second remaining part of the second portion that does not include the second part.

20. The apparatus according to claim 17, wherein the processing circuitry is further configured to
  determine a first position for the first portion in the third scatter sinogram;
  determine a second position for the second portion in the third scatter sinogram; and
  copy the first portion at the first position and the second portion at the second position, wherein
  a size of the third scatter sinogram is equal to a size of the first scatter sinogram and equal to a size of the second scatter sinogram.

* * * * *